(12) United States Patent
Foley

(10) Patent No.: US 9,283,019 B2
(45) Date of Patent: Mar. 15, 2016

(54) FLEXIBLE GUIDE WIRE

(75) Inventor: Kevin T. Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 689 days.

(21) Appl. No.: 13/155,817

(22) Filed: Jun. 8, 2011

(65) Prior Publication Data

US 2012/0316608 A1 Dec. 13, 2012

(51) Int. Cl.
| | | |
|---|---|---|
| *A61B 17/58* | (2006.01) |
| *A61B 17/60* | (2006.01) |
| *A61F 2/00* | (2006.01) |
| *A61B 17/88* | (2006.01) |
| *A61B 19/00* | (2006.01) |

(52) U.S. Cl.
CPC ....... *A61B 17/8897* (2013.01); *A61B 2019/307* (2013.01)

(58) Field of Classification Search
CPC ........... A61B 17/0401; A61B 17/8897; A61B 17/8875; A61B 17/8861
USPC ........ 606/86 R, 103, 104, 232, 319; 600/585; 81/461
See application file for complete search history.

(56) References Cited

U.S. PATENT DOCUMENTS

| | | | |
|---|---|---|---|
| 4,798,598 A | | 1/1989 | Bonello et al. |
| 5,141,520 A | * | 8/1992 | Goble et al. ................ 606/232 |
| 5,156,616 A | * | 10/1992 | Meadows et al. ............ 606/232 |
| 5,165,421 A | | 11/1992 | Fleischhacker et al. |
| 5,465,421 A | | 11/1995 | McCormick et al. |
| 5,611,801 A | * | 3/1997 | Songer ......................... 606/103 |
| 5,876,373 A | | 3/1999 | Giba et al. |
| 6,106,489 A | | 8/2000 | Gibertoni et al. |
| 6,368,326 B1 | * | 4/2002 | Dakin et al. ................. 606/103 |
| 6,520,907 B1 | | 2/2003 | Foley et al. |
| 6,530,913 B1 | | 3/2003 | Giba et al. |
| 6,638,268 B2 | | 10/2003 | Niazi |
| 6,685,696 B2 | | 2/2004 | Fleischhacker et al. |
| 7,008,422 B2 | | 3/2006 | Foley et al. |
| 7,056,314 B1 | | 6/2006 | Florio et al. |
| 7,226,410 B2 | | 6/2007 | Long |
| 7,591,823 B2 | * | 9/2009 | Tipirneni ..................... 606/103 |
| 8,137,381 B2 | * | 3/2012 | Foerster et al. .............. 606/232 |
| 8,425,536 B2 | * | 4/2013 | Foerster et al. .............. 606/139 |
| 2001/0021831 A1 | | 9/2001 | Fleischhacker et al. |
| 2004/0054322 A1 | | 3/2004 | Vargas |
| 2005/0043742 A1 | * | 2/2005 | Bruneau et al. ................ 606/99 |
| 2006/0200048 A1 | * | 9/2006 | Furst et al. ................... 600/585 |
| 2007/0010162 A1 | | 1/2007 | Chen |
| 2007/0049847 A1 | | 3/2007 | Osborne |
| 2007/0185415 A1 | | 8/2007 | Ressemann et al. |
| 2008/0091170 A1 | | 4/2008 | Vargas et al. |
| 2008/0097436 A1 | * | 4/2008 | Culbert et al. ................. 606/61 |
| 2008/0147128 A1 | * | 6/2008 | Fritzinger .................... 606/304 |
| 2008/0161855 A1 | * | 7/2008 | Serhan et al. ................ 606/246 |
| 2008/0275458 A1 | * | 11/2008 | Bleich et al. ................. 606/103 |
| 2009/0275994 A1 | * | 11/2009 | Phan et al. .................. 606/86 A |
| 2010/0042106 A1 | * | 2/2010 | Bryant et al. ................ 606/103 |

* cited by examiner

*Primary Examiner* — Kevin T Truong
*Assistant Examiner* — Si Ming Ku

(57) ABSTRACT

The present invention relates generally to flexible guide wires, and, more particularly, to a flexible guide wire that can be attached to a surgical site and pulled taut to provide a guide for the introduction of instruments and implants to the surgical site, but cannot be pushed towards the surgical site without the wire bending so that there is no advancement of the tip of the flexible guide wire further into the surgical site or bony structure.

4 Claims, 9 Drawing Sheets

FLEXIBLE GUIDE WIRE

FIELD OF THE INVENTION

The present invention relates generally to flexible guide wires, and, more particularly, to a flexible guide wire that can be anchored or attached to a surgical site and pulled taut to provide a guide for the introduction of surgical instruments and implants to the surgical site. When the flexible guide wire is pushed towards the surgical site, the wire will simply bend or coil without advancing the tip of the flexible guide wire further into the surgical site. While the present invention will be described for use in spinal surgery, the flexible guide wire will also find use in other orthopedic surgical areas as well.

BACKGROUND

In the field of orthopedic surgery, and particularly spinal surgery, it is well known to use a guide wire or what is also called a 'K' wire to provide a guide for the insertion of surgical instruments or implants into a surgical site. In some cases, this is a typical open surgical procedure where an incision has been made to fully open the surgical site to allow for the introduction of surgical tools and implants. In other cases, the surgeon desires to perform a minimal access surgical procedure where only a very small incision or access opening is created into which the surgeon would like to introduce the surgical tools, such as a surgical drill, tap, or other surgical instrument, to the surgical site. The surgeon additionally would like to introduce into this minimal access site the implants necessary to complete the surgical procedure.

Typically, when using such a relatively stiff guide wire, the surgeon would advance a sufficient length of the guide wire into the surgical site to make contact with the bony structure or soft tissue where the surgeon wishes to perform a surgical procedure. When performing spine surgery, the surgeon generally advances a variety of surgical tools over the guide wire, such as a drill and a tap for creating a threaded hole, and then the surgeon typically advances a cannulated bone screw over the guide wire for attachment to the bony structure or tissue. However, it is important for the surgeon to hold the guide wire firm against any further forward movement into the bony structure or tissue while advancing such instruments or implants along the guide wire to prevent the tip of the guide wire from advancing further into the surgical site and into unwanted areas of the bony structure or tissue such as the spinal cord, nerves, or blood vessels. Such unwanted advancement of the guide wire may cause punctures or other invasions that would require the surgeon to immediately remove such hardware to repair any damage, thus causing unnecessary pain, time, or expense in treating the patient. There are also many different spinal and orthopedic surgical procedures where a guide wire could be used and in many of these situations it would be desirable to control the tip of the guide wire in such a fashion that a surgeon could guarantee that the tip will not travel to unwanted anatomical locations.

SUMMARY

In one aspect of the present invention, a flexible guide wire has a distal tip for attachment to the bony structure or tissue within, at, or near a surgical site of a patient. The tip of the guide wire has a plurality of threads about its circumference to aid in attachment of the tip to any bony structure or tissue. The guide wire is sufficiently flexible such that with the tip engaged in the bony structure or tissue, any pushing on the proximal end of the guide wire will cause the guide wire to bend or coil without any further advancement of the tip. If the proximal end of the guide wire is pulled proximally away from its distal tip which is anchored any/or imbedded in the bony structure or tissue, the guide wire becomes taut and instruments and implants may be advanced along the guide wire for introduction into the surgical site. A sheath may be provided to assist in the initial introduction of the flexible guide wire into the surgical site. The sheath may also be utilized to assist in threading the tip of the flexible guide wire into the bony structure or tissue. The sheath would then be removed to allow the surgeon or other user to utilize the flexible guide wire to advance the instruments and implants into the surgical site.

In another aspect of the present invention, a flexible guide wire is provided wherein the distal tip of the guide wire has a plurality of ridges about its circumference to aid in the attachment of the tip to the bony structure or tissue. A sheath is provided to assist in the initial introduction of the flexible guide wire into the surgical site and to anchor or imbed the distal tip of the flexible guide wire into the bony structure or tissue of the intended surgical site. The sheath may have a flattened proximal end or a separate blunt head may also be passed over the flexible guide wire proximal to the sheath to allow for a mallet or hammer to be used to advance the sheath and guide wire into the bony structure or tissue to attach the tip of the flexible guide wire to such bony structure or tissue. The sheath or sheath and blunt head would then be removed to allow the surgeon or other user to pull the flexible guide wire taut to advance the instruments or implants along the guide wire for use within the surgical site.

In yet another aspect of the invention, a flexible guide wire has a distal tip and a flexible wire, wherein the flexible wire is constructed and configured to be sufficiently flexible to bend if the proximal end of the wire is pushed towards its distal tip. The flexible wire is manufactured out of metal or other flexible material having sufficient strength to allow the wire to be pulled taut when its distal tip is embedded within a patient's bony structure or tissue and allow for the introduction of instruments and implants over such taut wire and into a surgical site. In some embodiments, the tip or wire is manufactured out of a resorbable material such that if the tip or a portion of the wire is left in the body after the surgery is completed, such material will be resorbed into the bony structure or tissue without any damage to the patient.

In yet another aspect of the invention, a flexible guide wire has a distal tip and a flexible wire with the flexible wire provided with a calibrated breaking point at its distal end adjacent the distal tip. The calibrated breaking point of the wire is determined to allow the wire to be pulled taut by the surgeon or other user once the distal tip is attached to the bony structure or tissue to allow the surgeon or other user to introduce instruments or implants over the wire to complete the surgical procedure. However, if the proximal end of the flexible wire is sharply pulled taut, the wire will break at the calibrated break point to allow the flexible wire to be withdrawn from the surgical site while leaving the distal tip embedded within the bony structure or tissue.

Yet another aspect of the invention includes a method of introducing a flexible guide wire into a surgical site within a body to allow for the introduction of surgical instruments and implants over the guide wire and into the surgical site. The method includes creating an incision in the body to provide access to a surgical site. A flexible guide wire having 1) a flexible wire with a proximal end and a distal end, and 2) a distal tip attached to the distal end of the flexible wire, the distal tip attachable to or near the surgical site, is prepared for introduction and advancement through this incision. A sheath having a proximal end and a distal end and configured to pass over the flexible wire until the distal end is in contact with the distal tip of the flexible guide wire is associated with or passed over the flexible guide wire. The flexible guide wire and sheath are introduced through the incision to attach the distal tip of the flexible guide wire to the surgical site. The sheath is then removed from about the flexible wire leaving the flexible wire and distal tip attached to the surgical site. The flexible wire is pulled taut from the proximal end of the flexible wire and at least one surgical instrument or implant is introduced over the taut flexible wire to the surgical site. Then the flexible wire is removed from the surgical site by sharply pulling on the proximal end of the flexible wire.

These and other aspects, forms, objects, features, and benefits of the present invention will become apparent from the following detailed description and drawings.

BRIEF DESCRIPTION OF THE DRAWINGS

In the accompanying drawings, which are incorporated in and constitute a part of the specification, embodiments of the present invention are illustrated, which together with a general description of the invention set forth above, and the detailed description set forth below, serve to exemplify the embodiments of the invention. The components in the Figures are not necessarily to scale, emphasis instead being placed upon illustrating the principles of the invention and, in the Figures, like reference numerals designate corresponding parts throughout the different views.

DETAILED DESCRIPTION

Figure 1:
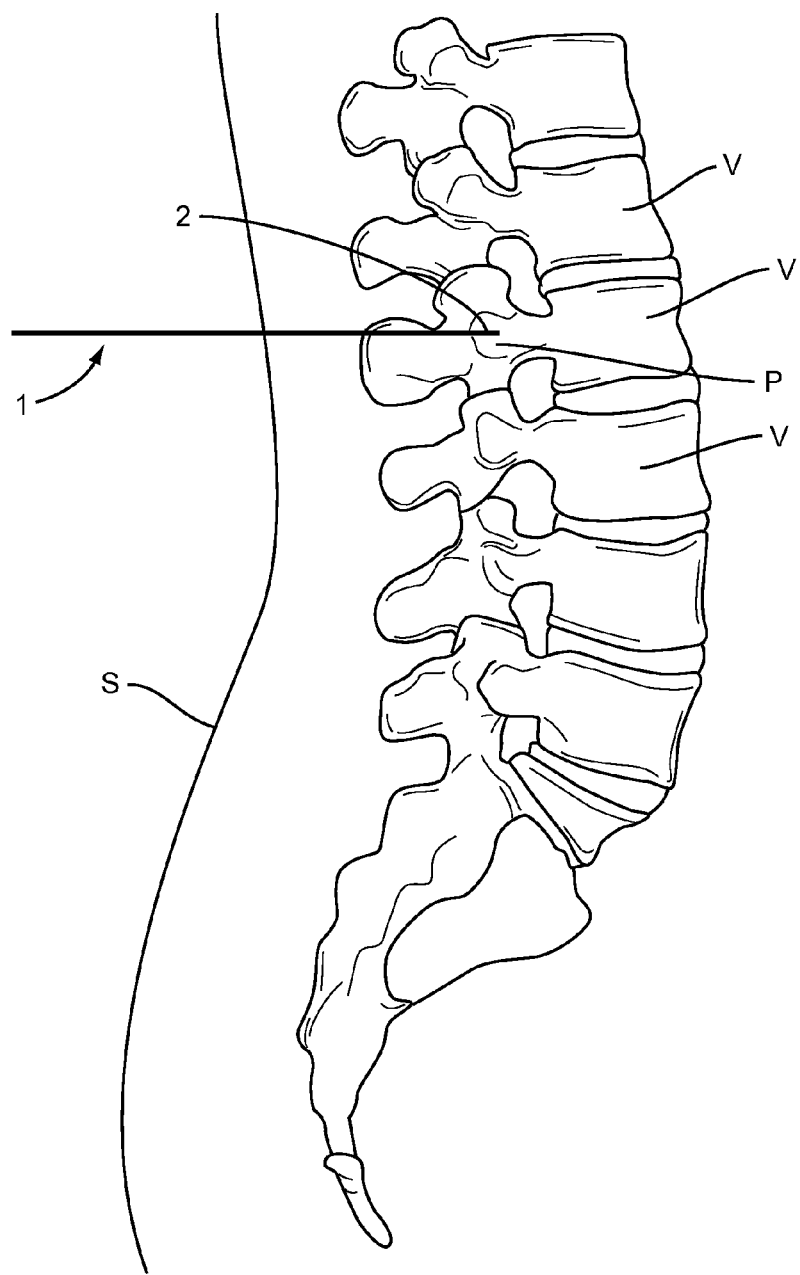
FIG. 1 is a side view of a number of vertebrae of the spinal column showing the prior art guide wire being positioned through the skin with its tip placed adjacent the pedicle of a vertebral body.

For the purposes of promoting an understanding of the principles of the invention, reference will now be made to the embodiments illustrated in the drawings and specific language will be used to describe these embodiments. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

FIG. 1 illustrates the prior art guide wire 1 passing through the skin S of a human patient with the distal tip 2 of guide wire 1 being placed adjacent the pedicle P of a vertebra V of a spinal column. The guide wire 1 is a relative stiff wire which is then utilized to guide surgical instruments such as drills and taps into a surgical site to allow a surgeon to perform surgical procedures. For discussion purposes with respect to the present disclosure, a spinal surgical procedure will be illustrated wherein a surgeon wishes to locate a surgical site on the pedicle of a spinal column. The surgeon will drill and tap a hole through the pedicle and into the vertebra to allow for the insertion of a spinal implant, such as a pedicle screw. When using such a guide wire, the drill, tap, and spinal implant are all cannulated to allow them to be passed over the guide wire to access the surgical site. A difficulty with the prior art relatively stiff guide wire is that it is necessary to hold the guide wire steady against any further proximal or distal movement during the procedures of advancing such instruments or implants along to guide wire for application at the surgical site. If the relatively stiff guide wire of the prior art is allowed to pull away from the pedicle in a proximal direction, it may be possible to misdirect the instruments or spinal implants causing the surgeon to repeat the procedure to more accurately place such instruments or spinal implant to complete the surgical procedure. If the guide wire is allowed to advance further into the surgical site while advancing the instruments or spinal implants into the surgical site, the distal tip of the guide wire may travel into unwanted areas of the human anatomy, such as into the spinal column, nerves, or blood vessels, thereby possibly causing harm to a patient.

It is important to note that such guide wires, including the flexible guide of the present invention, can realistically be used to guide instruments and implants into many locations within the body to allow for a surgeon to complete a surgical procedure therein. The present disclosure is not meant to limit the use of the flexible guide wire to the disclosed surgical application described herein. Furthermore, with respect to this disclosure the use of the words "proximal" and "distal" are meant to refer to directions either away from the surgical site or towards the surgical site, respectively.

Figure 2:
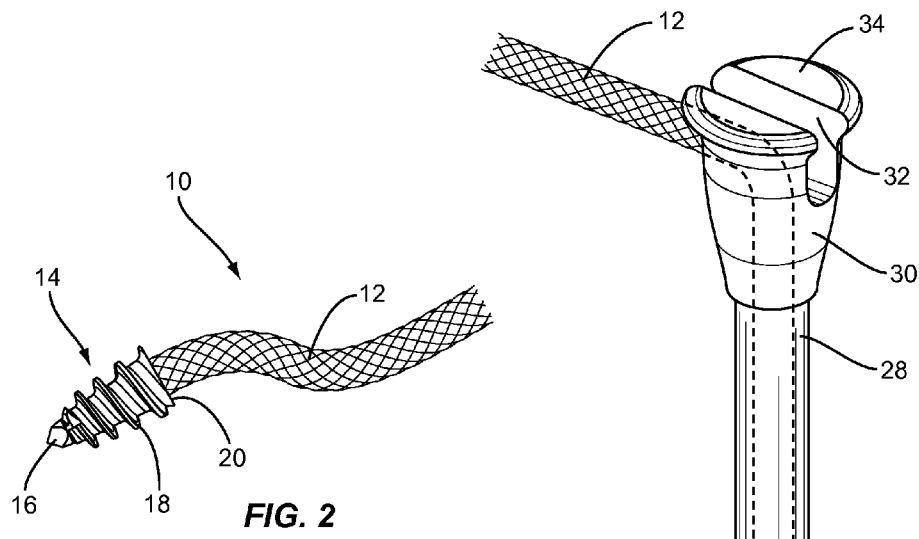
FIG. 2 is a side view of a distal portion of the flexible guide wire according to one embodiment of the present invention showing a threaded distal tip and distal portion of the flexible wire.

FIG. 2 illustrates a portion of the flexible guide wire 10 of the present invention having a flexible wire 12 and a distal tip 14. The distal tip 14 is shown having a slightly larger diameter than the flexible wire 12 and is provided with a distal point 16 and external threads 18. The distal point 16 and threads 18 need to be sharp enough to be able to thread the distal tip 14 into a bony structure such as a pedicle. The flexible wire 12 can be a single wire or a braided set of wires sufficiently strong so as to allow for its proximal end (not shown) to be pulled taut to allow for the insertion of the surgical instruments needed to drill and tap a hole through the pedicle and into the vertebra. A small shoulder 20 is provided on the proximal end of the distal tip 14 which will be described in more detail below. The flexible wire 12 can be of any length sufficient to extend out of the surgical site and body to allow the surgeon to insert surgical instruments and implants over the wire outside of the body to guide the same into the surgical site for completing the necessary surgical procedures. The flexible wire 12 may be manufactured out of any appropriate medical grade materials, such as metals, including but not limited to titanium, stainless steel, cobalt-chrome alloys; fabric; natural or manmade fibers, including but not limited to nylon, polyester, polyethylene, polyarylarylketone (such as polyetheretherketone (PEEK)); or any other medical grade material that is sufficiently strong and flexible.

Figure 3:
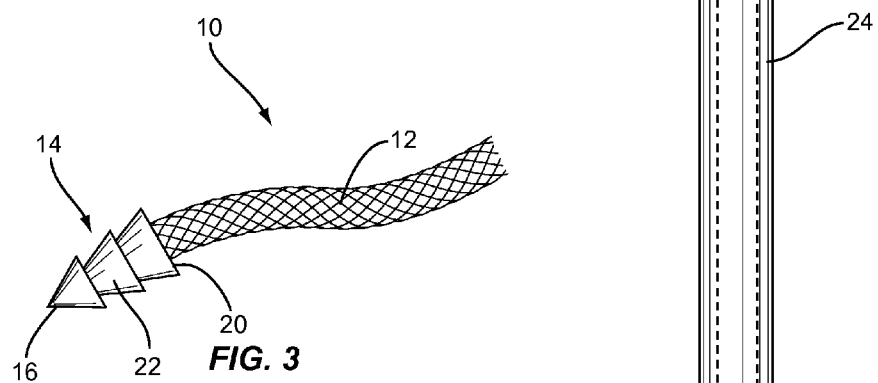
FIG. 3 is a side view of a distal portion of the flexible guide wire according to another embodiment of the present invention showing a ridged distal tip and distal portion of the flexible wire.

FIG. 3 illustrates a portion of the flexible guide wire 10 of an alternate embodiment having a flexible wire 12 and a distal tip 14. The distal tip 14 is shown having a slightly larger diameter than the flexible wire 12 and is provided with a distal point 16 and concentric ridges 22. A small shoulder 20 is provided on the proximal end of the distal tip 14 which will be described in more detail below. The ridges 22 are provided to allow the distal tip 14 to be pushed into the bony structure or tissue to attach the flexible guide wire 10 to the surgical site, as will be described in greater detail below.

Figure 4:
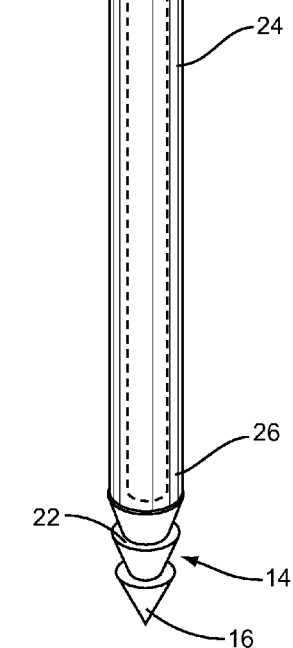
FIG. 4 is a side perspective view of the flexible guide wire shown in FIG. 3 with a sheath and blunt head provided over the flexible wire.

FIG. 4 illustrates the flexible guide wire 10 of FIG. 3 in use with an introduction sheath 24. The sheath 24 is configured to slide over the flexible wire 12 until a distal end 26 of the sheath 24 is in contact with or engages the shoulder 20 of the distal tip 14. As shown in FIG. 4, a blunt head 30 may also be present and is configured to slide over the flexible wire 12 until it is adjacent a proximal end 28 of the sheath 24. The blunt head 30 has a slot 32 and a flattened top 34. The slot 32 provides a pathway for the flexible wire 12 to pass through so that a small mallet or hammer can be used to strike or otherwise impact the flat top 34 to apply longitudinal force in a distal/axial direction along the sheath 24 and distal tip 14 of the flexible guide wire 10 to embed the distal tip 14 within the bony structure or tissue of the surgical site without impacting, or with minimal impact to, the flexible wire 12. By minimal impact, it is meant that only incidental impact without damage to the flexible wire 12 is applied. The blunt head 30 and sheath 24 may be removed from the flexible guide wire 10 as will be further described below.

Instead of providing a blunt head 30, the proximal end 28 of the sheath 24 could simply be slotted so that a mallet could be used directly on its proximal end to apply the force necessary to embed the distal tip 14 of the flexible guide wire 10 into the bony structure or tissue of the surgical site without impacting, or with minimal impact to, the flexible wire 12. Furthermore, the proximal end 28 of the introduction sheath 24 could also be provided with an enlarged end and a slot to allow the mallet to strike the proximal end 28 as necessary to embed the distal tip 14 of the flexible guide wire 10 into the bony structure or tissue of the surgical site.

Figure 5:
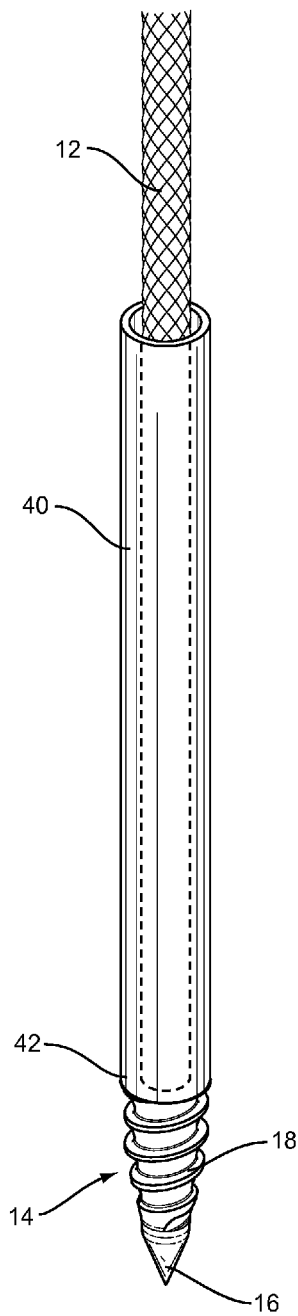
FIG. 5 is a side perspective view of the flexible guide wire shown in FIG. 2 with a sheath provided about the flexible wire.
Figure 6:
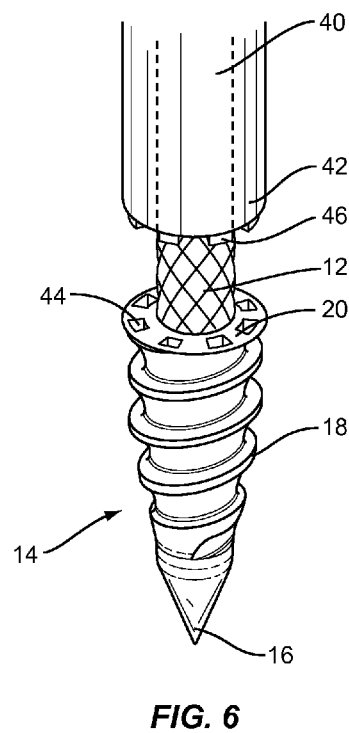
FIG. 6 is a partial side perspective view of the flexible guide wire shown in FIGS. 2 and 5 showing the distal tip of the guide wire and sheath to illustrate one embodiment of the interconnection between the guide wire and sheath.
Figure 7:
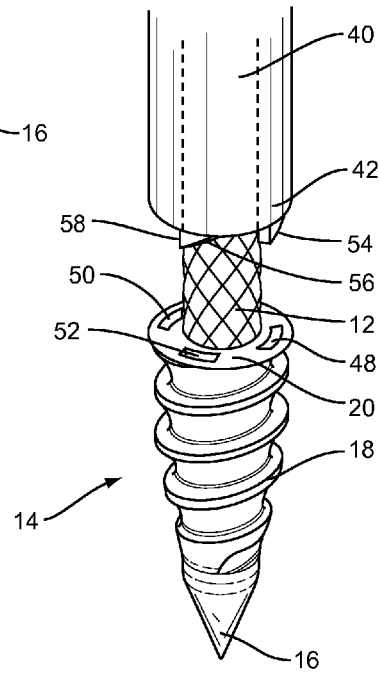
FIG. 7 is a partial side perspective view of the flexible guide wire shown in FIGS. 2 and 5 showing the distal tip of the guide wire and sheath to illustrate another embodiment of the interconnection between the guide wire and the sheath.

FIGS. 5 through 7 illustrate the flexible guide wire 10 of FIG. 2 in use with an introduction sheath 40. The sheath 40 is configured to slide over the flexible wire 12 until the distal end 42 of the sheath 40 is in contact with or otherwise engages the shoulder 20 of the distal tip 14 of the flexible guide wire 10. In the illustrated embodiment, the distal tip 14 is provided with external threads 18 for attachment to the bony structure or tissue of the surgical site.

FIG. 6 illustrates one embodiment of the flexible guide wire 10 wherein the shoulder 20 of the distal tip 14 is provided with a plurality of generally rectangular indentations 44 and the distal end 42 of the sheath 40 is provided with a plurality of depending generally rectangular projections 46 configured to engage the indentations 44. When the sheath 40 is engaged or mated against the shoulder 20 of the distal tip 14 and the projections 46 engage the indentations 44, the sheath 40 can be used to rotate the distal tip 14 and flexible guide wire 10 to thread the distal tip 14 into the bony structure or tissue of the surgical site.

FIG. 7 illustrates another embodiment of the flexible guide wire 10 wherein the shoulder 20 of the distal tip 14 is provided with a plurality of ramps 48 wherein each ramp has a slanted surface 50 and a generally horizontal wall 52. The distal end 42 of the sheath 40 is provided with a plurality of depending projections 54, each projection 54 having a slanted surface 56 and generally horizontal wall 58 matching those surfaces and walls of the ramps 48 of the shoulder 20. When the sheath 40 is engaged or mated against the shoulder 20 of the distal tip 14 and the projections 54 engage the ramps 48, the sheath 40 can be used to rotate the distal tip 14 and flexible guide wire 10 in a clockwise direction to thread the distal tip 14 into the bony structure of the surgical site. However, if the sheath 40 is rotated in a counterclockwise direction, the sheath 40 separates from the distal tip 14 leaving the distal tip 14 threaded into the bony structure or tissue. Note that the embodiment of the distal tip 14 illustrated in FIG. 3 may also be used with sheath 40 that engages the shoulder 20.

Figure 8:
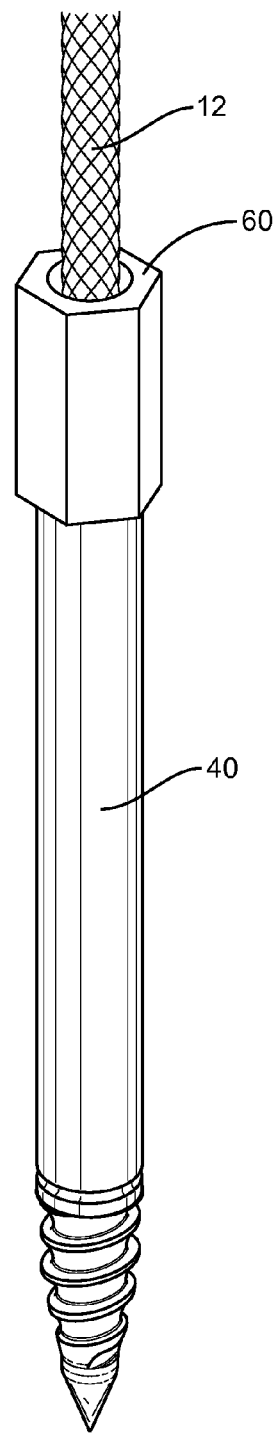
FIG. 8 is a side perspective view of the flexible guide wire shown in FIG. 5 where are alternate embodiment of the sheath is shown.

FIG. 8 illustrates the flexible guide wire 10 of FIG. 5 in use with an alternate embodiment of the introduction sheath 40. In this embodiment, the distal tip 14 is provided with external threads 18 for attachment to the bony structure or tissue of the surgical site. The sheath 40 is provided with a knob 60 which can be used to rotate the sheath 40 either by hand or with the aid of wrench (not shown) to thread the distal tip 14 of the guide wire 10 into the bony structure or tissue of the surgical site. The knob 60 is illustrated with a hexagonal shape, but any shape may be configured without departing from the spirit and scope of the invention.

Figure 9:
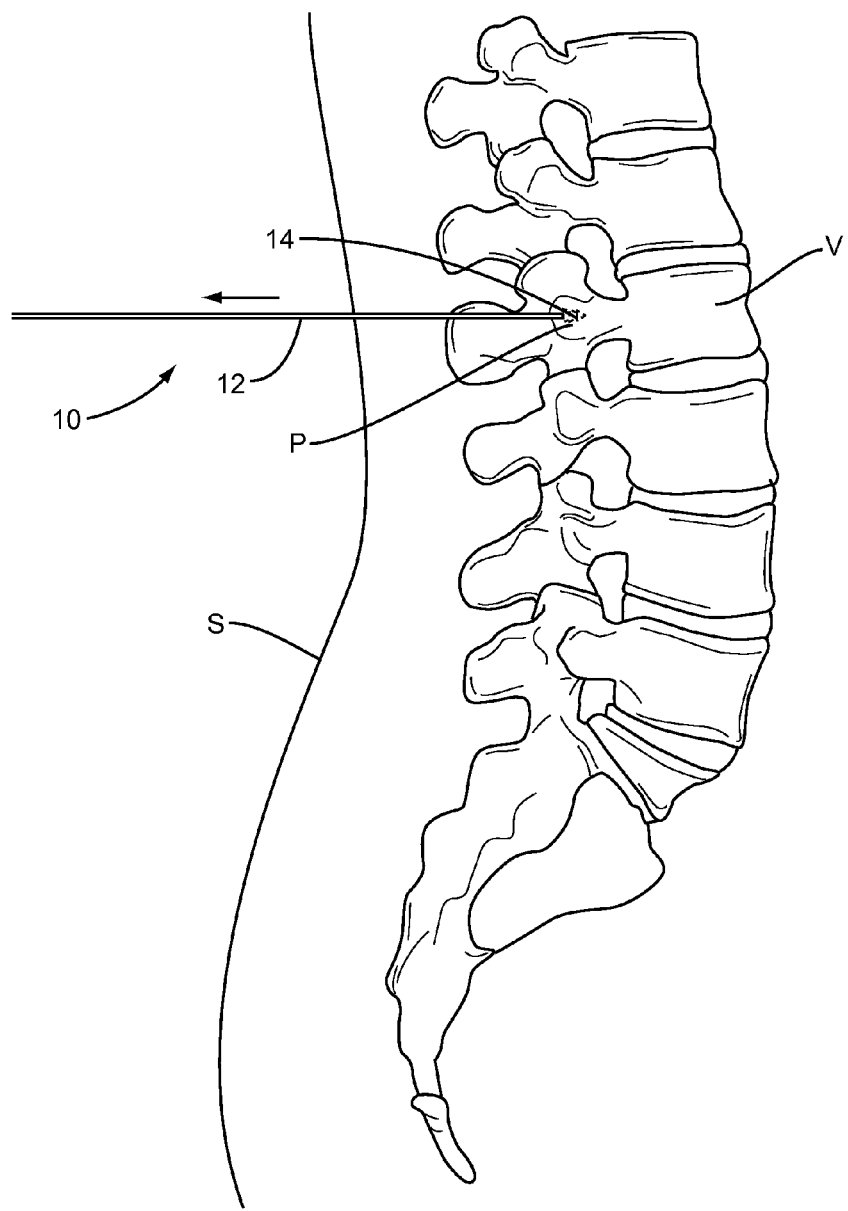
FIG. 9 is a side view similar to FIG. 1 showing the flexible guide wire attached to a vertebra with an arrow illustrating the flexible guide wire being pulled in a proximal direction to provide a taut guide wire for guiding instruments and implants along the guide wire for introduction into a surgical site.
Figure 10:
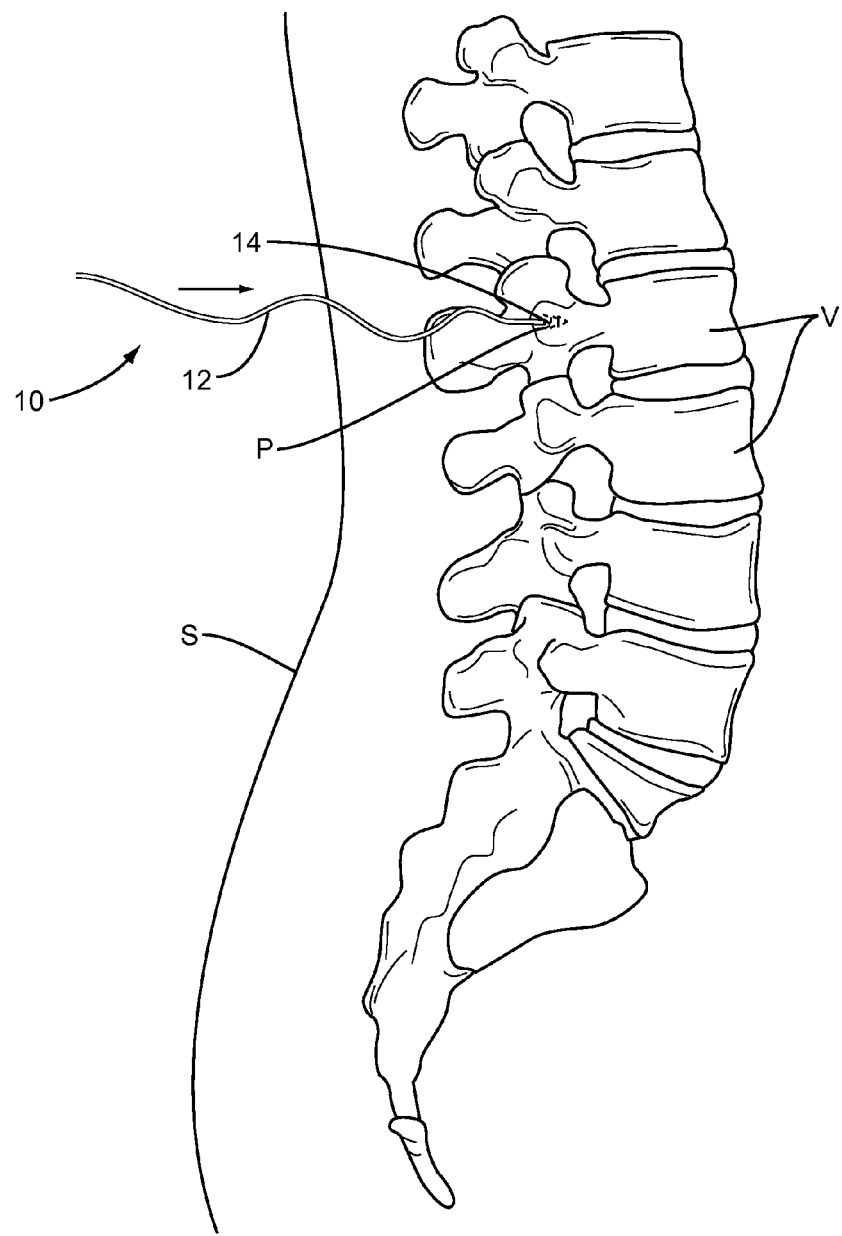
FIG. 10 is a side view similar to FIGS. 1 and 9 showing the flexible guide wire attached to a vertebra with an arrow illustrating the flexible guide wire being pushed in a distal direction to show the flexibility of the wire with respect to the distal tip of the guide wire.

FIGS. 9 and 10 illustrate use of the flexible guide wire 10 in greater detail. In FIG. 9, the flexible guide wire 10 is shown with its distal tip 14 embedded within the pedicle P of a vertebra V. The flexible guide wire 10 and sheath 24 or 40 would have been used to install the flexible guide wire 10 through the skin S and into the pedicle P. The sheath 24 or 40 would then have been removed from the surgical site. This procedure could be done via an open incision that would provide a generally large opening in the skin S to allow for the introduction of the flexible guide wire 10 into the surgical site. Alternatively, the procedure could be done in a minimally invasive manner wherein only a small incision is made through the skin S to allow for the introduction of the flexible guide wire 10 into the surgical site.

An arrow is shown in FIG. 9 depicting that a force is being applied to the flexible guide wire 10 to pull it taut to provide a guide for the introduction of instruments, such as those required to first drill a hole through the pedicle and into the vertebral body of the vertebra and then to tap such hole to provide internal threads for the introduction of a pedicle screw, such screw being commonly known in the industry.

The pedicle screw would also be cannulated to allow the screw to be advanced along the flexible wire 12 and into the surgical site.

In FIG. 10, the flexible guide wire 10 is shown with its distal tip 14 embedded within the pedicle P of a vertebra V as is shown in FIG. 9. However, in FIG. 10 an arrow is shown depicting that a force is being applied to the flexible wire 12 in a direction towards the surgical site such that the flexible wire 12 will bend or coil in a manner that does not introduce any significant distal force on the distal end 14 of the flexible guide wire 10.

Figure 11:
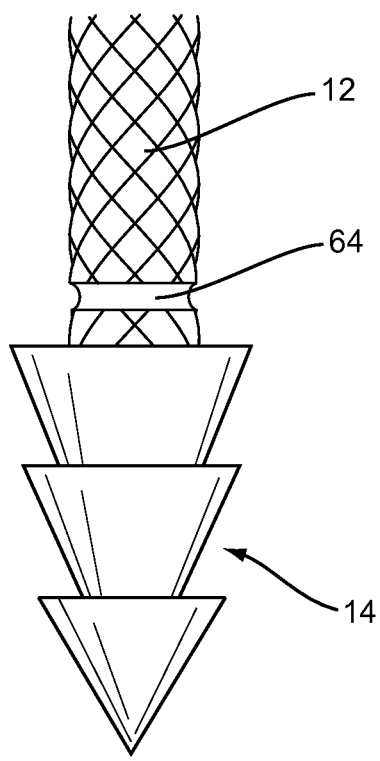
FIG. 11 is a partial side view of the distal end of the flexible guide wire illustrating the calibrated breaking point of the wire adjacent the distal tip of the flexible guide wire.

FIG. 11 illustrates an embodiment of the flexible guide wire 10 in which a calibrated breaking point 64 is provided on the flexible wire 12 at a position adjacent or near the distal tip 14. When the surgical procedure is completed, a surgeon or other user could apply a sharp tug on the proximal end of the flexible wire 12 to break the flexible wire 12 away from the distal tip 14. It may not be necessary to provide such a breaking point because after advancing instruments and spinal implants over the flexible wire 12, the surgeon or other user may be able to dislodge the flexible wire 12 and distal tip 14 with a sharp tug on the flexible wire 12 in a proximal direction. However, it may be desirable to provide the calibrated breaking point 64 to easily remove the flexible wire 12 from the surgical site. Although FIG. 11 illustrates use of the calibrated breaking point 64 with the distal tip 14 embodiment of FIG. 3 having concentric ridges, the calibrated braking point 64 may also be used with the distal tip 14 embodiment of FIG. 2 having external threads.

The distal tip 14 can be made out of any appropriate medical grade materials, including but not limited to metals such as titanium, stainless steel, cobalt-chrome alloys; or polymers, such as nylon, polyester, polyethylene, or polyarylarylketone (such as polyetheretherketone (PEEK)). It may also be desirable to manufacture the flexible wire 12 or the distal tip 14 out of a resorbable material such that if any portion of the distal tip 14 or flexible wire 12 is left in the surgical site, these materials will be slowly absorbed with the body without causing any harm to the surrounding tissue or patient as a whole.

In operation, the flexible guide wire 10 is introduced into a surgical site to allow for the introduction of instruments or implants over the flexible guide wire 10. The surgeon creates an incision in the body to provide access to the surgical site. The flexible guide wire 10 described above, including a flexible wire 12 with a proximal end and a distal end, and with a distal tip 14 attached to the distal end, provided and is prepared to be introduced through the incision. The distal tip 14 is attachable to or near to the surgical site.

In some embodiments, the sheath 24 or 40, having a proximal end and a distal end, is passed over the flexible wire 12 until the distal end is in contact with or engages the distal tip 14. The flexible guide wire 10 and the sheath 24 or 40 are introduced through the incision to attach the distal tip 14 to or near the surgical site. Then the sheath 24 or 40 is removed from about the flexible guide wire 10, leaving the flexible wire 12 and the distal tip 14 attached to or near the surgical site.

The surgeon or other user pulls the flexible wire 12 taut from the proximal end of the flexible wire 12 to introduce one or more surgical instruments or implants over the flexible wire 12 to the surgical site. When the procedure is complete, the surgeon or other user removes the flexible wire 12 from the surgical site by sharply pulling on the proximal end of the flexible wire 12. This may be, but need not be, accomplished via the calibrated breaking point 64, described above. In some embodiments, the flexible wire 12 is separated from the distal tip 14 and the distal tip 14 is left within the surgical site. In other embodiments, the distal tip 14 and the flexible wire 12 are removed from the surgical site.

The instruments to be introduced over the flexible wire 12 include any instruments needed or desired to perform procedures at the surgical site, including, but not limited to, bone drill (e.g., hand, motorized, or hydraulic), bone tap, and implant driver. The implants to be introduced over the flexible wire 12 include any implants needed or desired to be left at the surgical site, including, but not limited to, screws, screw heads, and connecting elements.

In some embodiments in which the distal tip 14 is provided with threads, introducing the flexible guide wire 10 and sheath 24 or 40 includes rotationally attaching the distal tip 14 to the surgical site. In some embodiments in which the distal tip 14 is provided with concentric ridges, introducing the flexible guide wire 10 and sheath 24 or 40 includes longitudinally or axially pushing, with steady or with periodic force, on the sheath 24 or 40 from its proximal end.

In some embodiments, the described method is used to introduce a flexible guide wire 10 to a pedicle of a vertebra to allow for the introduction of a bone drill, bone tap, implant driver, and a threaded spinal implant over the guide wire to the pedicle. In this embodiment, the surgical site is the pedicle. The threaded spinal implant may be a pedicle screw. The bone drill and bone tap are used to create a threaded hole through the pedicle and into the vertebral body. The spinal implant is threaded into the threaded hole. In some embodiments with the pedicle as the surgical site, the distal tip 14 is dislodged from the pedicle by sharply pulling on the proximal end of the flexible wire 12.

Figure 12:
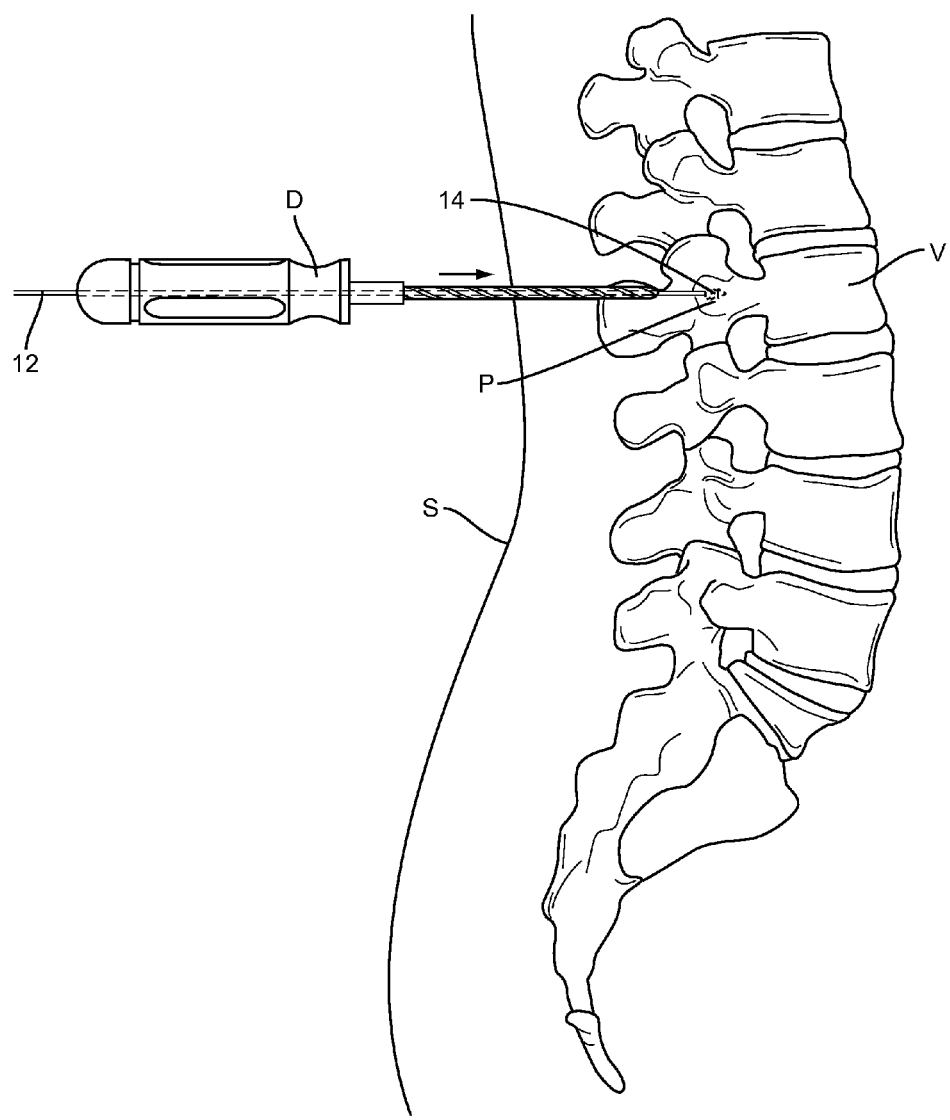
FIG. 12 is a side view similar to FIG. 9 showing an instrument being advanced along the taut guide wire to allow a surgeon or other user to perform a surgical procedure within a surgical site.
Figure 13:
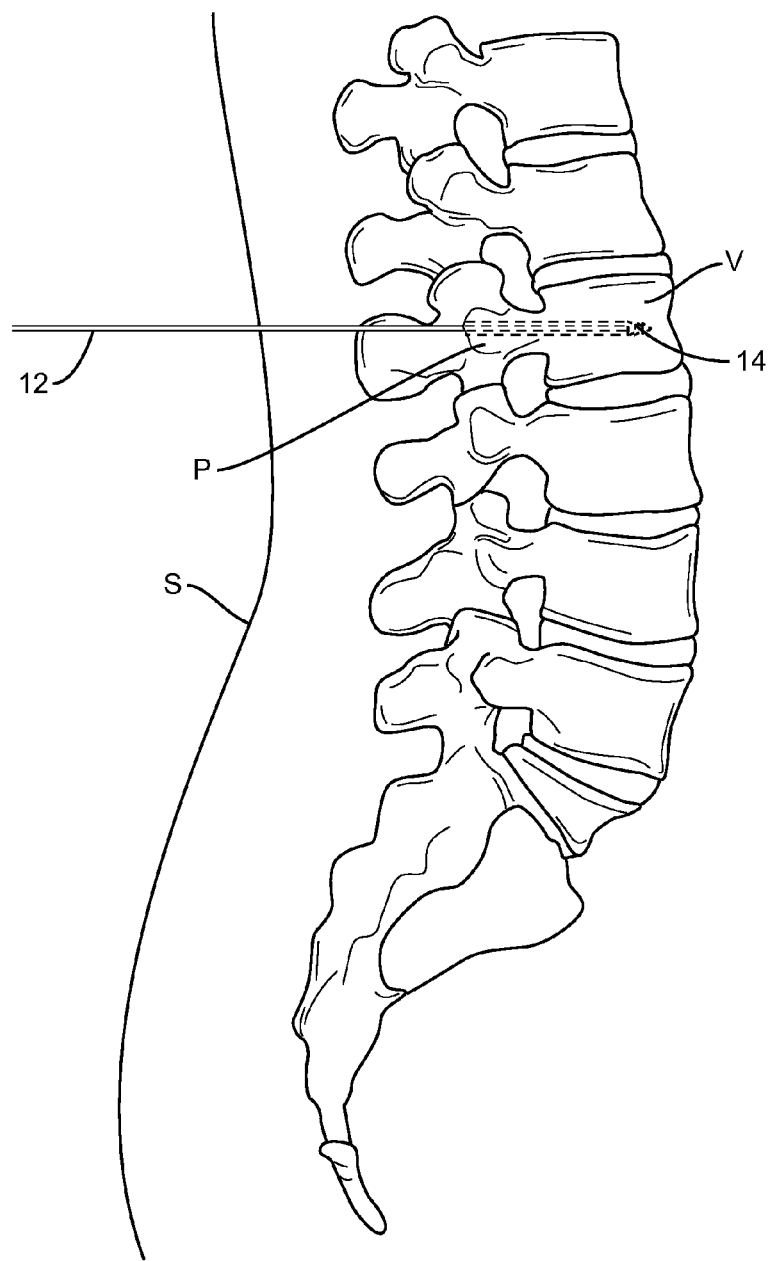
FIG. 13 is a side view similar to FIG. 9 showing the distal tip of the guide wire being positioned within a drilled hole through the pedicle and into a vertebra of the spinal column.

FIGS. 12 and 13 illustrate the surgical procedure of installing a pedicle screw through a pedicle and into the vertebral body of the vertebra. In FIG. 12, the flexible guide wire 10 of the present invention is shown with its distal tip 14 embedded within the pedicle P of the vertebra V. The flexible wire 12 is being held taut by the surgeon or other user lightly pulling on the proximal end of the flexible wire 12. A drill D is shown being advanced along the flexible wire 12 until the drill D contacts the pedicle P. The surgeon or other user would typically use fluoroscopic or other images to guarantee the correct trajectory for drilling through the pedicle P and into the vertebral body. A hand drill or a motorized drill or a hydraulic drill would be used to create the hole through the pedicle P and into the vertebral body V. All of these instruments are cannulated for use over standard guide wires. The distal tip 14 of the flexible guide wire 10 is sized such that the drill bit will advance over the distal tip 14. However, during the drilling process the guide wire may release itself from the pedicle allowing the drilling process to be completed without the flexible guide wire 10 in place.

FIG. 13 illustrates that once the drill has been removed from the surgical site, a second flexible guide wire 10 and sheath 24 or 40 can be introduced into the hole previously drilled through the pedicle P and into the vertebral body V. The distal tip 14 will now be embedded into the bottom of the previously drilled hole. The surgeon or other user would then once again hold the proximal end of the flexible wire 12 taut to allow for the introduction of a surgical tap to internally thread the hole. A spinal implant, e.g., a pedicle screw, would be then advanced along the taut flexible wire 12 to thread the pedicle screw into the vertebral body V to further the surgical procedure. The surgeon or other user would then pull sharply on the proximal end of the guide wire 10 to pull loose the embedded distal tip 14 of the flexible guide wire 10. Alternatively, the flexible guide wire 10 would include the calibrated break point 64 and the flexible wire 12 would separate from the distal tip 14 to remove the flexible wire 12 from the surgical site. The distal tip would remain inside the vertebral body. If the distal tip 14 were manufactured out of a resorbable material it would eventually be resorbed within the vertebral body. If not, the distal tip 14 would simply remain within the vertebral body not causing any harm or injury to the patient.

In summary of the procedure of this embodiment, a first flexible guide wire 10 is used for placement of the drill relative to the pedicle and a second flexible guide wire 10 is used for placement of the pedicle screw into and through the pedicle. A first surgical site is the pedicle, to which the drill is guided, and a second surgical site is the hole through the pedicle into the vertebral body into which the bone tap and the implant, the pedicle screw, are guided. The first and second flexible guide wire 10 may be the same or different devices.

Alternatively, the surgeon or other user would install the flexible guide wire 10 with a sheath 24 or 40 with axial or longitudinal force to embed the distal tip 14 of the flexible guide wire 10 to a position shown in FIG. 13. The surgeon or other user would then hold the proximal end of the flexible wire 12 taut while advancing the instruments and spinal implants along the guide wire to perform the surgical procedures discussed above. Because the instruments and implants need not be advanced over the distal tip 14 in this situation, the distal tip 14 could have a larger diameter to provide additional external threads 18 or concentric ridges 22 for a more secure attachment to the bony structure or tissue. The cannulated instruments and implants would slide over the flexible wire 12 to advance such tools to the surgical site; however, such tools would not advance over the distal tip 14 embedded within the vertebral body V. The flexible guide wire 10 would be removed from the surgical site after completion of all of the surgical procedures to install the pedicle screw in the same manners as discussed above.

These procedures may be performed on a living human patient or animal, or may be performed on a non-living substrate, such as a model constructed from sawbones, ceramic, plastic, or any other material, or a cadaver, or a non-living animal substrate, or any other non-living substrate. These procedures may be used for treatment, training, research, development, demonstration, or any other purpose.

While the invention has been illustrated and described in detail in the drawings and foregoing description, the same is to be considered as illustrative and not restrictive in character; it being understood that only the preferred embodiments have been shown and described and that all changes and modifications that come within the spirit of the invention are desired to be protected. For example, the distal tip 14 may have other attachment mechanisms than threads or concentric ridges, such as clips, non-concentric ridges, non-circumferential ridges, spikes, expandable features, or other attachment mechanisms that are apparent to one of skill in the art. The flexible guide wire 10 may be introduced through the incision without the presence of a sheath.

Additional advantages and modifications will readily appear to those skilled in the art. Therefore, the invention in its broader aspects is not limited to the specific details, representative apparatus and methods of use, and illustrative examples shown and described. Accordingly, departures may be made from such details without departing from the spirit or scope of the applicant's general or inventive concept.

As used herein, the terms "having," "containing," "including," "comprising," and the like are open ended terms that indicate the presence of stated elements or features, but do not preclude additional elements or features. The articles "a," "an," and "the" are intended to include the plural as well as the singular, unless the context clearly indicates otherwise. The term "or" is used in its inclusive sense, meaning one or the other or both, unless the context indicates use in the exclusive sense. It is understood that all spatial references, such as "axial," longitudinal," "top," "bottom," "above," "below," and the like are for illustrative purposes only and can be varied within the scope of the disclosure. Further, terms such as "proximal," "distal," and the like are also used to describe various elements, regions, sections, directions, etc., and also are not intended to be limiting. Like terms refer to like elements throughout the specification.

I claim:

1. A method of introducing a flexible guide wire to a pedicle of a vertebra of the spinal column to allow for the introduction of a bone drill, bone tap, implant driver, and a threaded spinal implant over the guide wire and to the pedicle, comprising:

creating an incision in the body to provide access to a pedicle of a vertebra;

preparing a flexible guide wire to be introduced through the incision, the flexible guide wire comprising: a flexible wire with a proximal end and a distal end, and a distal tip attached to the distal end of the flexible wire, the distal tip attachable to the pedicle, wherein the distal end of the flexible wire is provided with a calibrated breaking point adjacent the distal tip;

passing a removable sheath having a proximal end and a distal end over the flexible wire such that the sheath extends from the proximal end to the distal end of the flexible wire and the sheath distal end is in contact with the distal tip of the flexible guide wire;

introducing the flexible guide wire and sheath through the incision to attach the distal tip of the flexible guide wire to the pedicle, applying an axial force to the sheath and the distal tip in a distal direction to embed the distal tip in tissue;

removing the sheath from about the flexible wire leaving the flexible wire and distal tip attached to the pedicle;

pulling the flexible wire taut from the proximal end of the flexible wire;

introducing the bone drill over the flexible wire to the pedicle to create a hole through the pedicle and into the vertebral body, then removing the bone drill;

guiding the bone tap over the flexible wire into the hole to create a threaded hole, then removing the bone tap;

introducing the threaded spinal implant over the flexible wire;

threading the threaded spinal implant through the pedicle and into the vertebral body with the implant driver; and removing the flexible wire from the pedicle by sharply pulling on the proximal end of the flexible wire to dislodge the distal tip from the pedicle.

2. The method of claim 1, wherein guiding the bone tap comprises introducing a second flexible guide wire, comprising a second flexible wire and a second distal tip, through the incision to attach the second distal tip to the bottom of the hole drilled through the pedicle and into the vertebral body, and wherein introducing the threaded spinal implant comprises introduction over the second flexible wire to thread the spinal implant through the pedicle and into the vertebral body; and removing the second flexible wire from the pedicle by sharply pulling on the proximal end of the second flexible wire.

3. The method of claim 2, wherein removing the second flexible wire from the pedicle comprises sharply pulling on the proximal end of the second flexible wire to separate the second flexible wire from the second distal tip at the calibrated breaking point to allow for the removal of the second flexible wire from the pedicle and leaving the second distal tip within the pedicle.

4. The method of claim 1, wherein the distal tip of the flexible guide wire is provided with external threads, and wherein introducing the flexible guide wire and sheath through the incision to attach the distal tip of the flexible guide wire comprises applying rotational force to the distal tip of the flexible guide wire.

* * * * *